(12) United States Patent
Dumontet et al.

(10) Patent No.: US 9,896,415 B2
(45) Date of Patent: Feb. 20, 2018

(54) CHALCONE DERIVATIVES HAVING AN ANTI-ALLERGIC ACTIVITY

(71) Applicants: UNIVERSITE CLAUDE BERNARD LYON I, Villeurbanne (FR); HOSPICES CIVILS DE LYON, Lyons (FR); CENTRE NATIONAL DE LA RECHERCHE SCIENTIFIQUE, Paris (FR)

(72) Inventors: Charles Dumontet, Venissieux (FR); Ahcene Boumendjel, Meylan (FR); Guillaume Monneret, Lyons (FR)

(73) Assignees: UNIVERSITE CLAUDE BERNARD LYON I, Villeurbanne (FR); HOSPICES CIVILS DE LYON, Lyon (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/781,145

(22) PCT Filed: Apr. 4, 2014

(86) PCT No.: PCT/FR2014/050816
§ 371 (c)(1),
(2) Date: Sep. 29, 2015

(87) PCT Pub. No.: WO2014/162106
PCT Pub. Date: Oct. 9, 2014

(65) Prior Publication Data
US 2016/0052881 A1    Feb. 25, 2016

(30) Foreign Application Priority Data
Apr. 5, 2013   (FR) ...................................... 13 53091

(51) Int. Cl.
*C07D 211/32*    (2006.01)
*C07D 211/22*    (2006.01)

(52) U.S. Cl.
CPC .......... *C07D 211/32* (2013.01); *C07D 211/22* (2013.01)

(58) Field of Classification Search
None
See application file for complete search history.

(56) References Cited

U.S. PATENT DOCUMENTS 6,462,075 B1    10/2002   Bowen et al.

FOREIGN PATENT DOCUMENTS

| FR | 2864956 A1 | 7/2005 |
|---|---|---|
| WO | 0198291 A2 | 12/2001 |
| WO | 2007083060 A2 | 7/2007 |
| WO | 2009126320 A1 | 10/2009 |

OTHER PUBLICATIONS

Liu, X. et al., Bioorg. Med. Chem. 2007 vol. 15 pp. 7021-7034.*
Boumiza et al.: "The basophil activation test by flow cytometry: recent developments in clinical studies, standardization and emerging perspectives", Clinical and Molecular Allergy, 2005, 3:9, available from: http://www.clinicalmolecularallergy.com/content/3/1/9.
Liu X L et al.: "Antiproliferative activity of chalcones with basic functionalities", Bioorganic & Medicinal Chemistry 15 (2007) 7021-7034.
International Search Report dated Jun. 3, 2014, corresponding to International Patent Application No. PCT/FR2014/050816.
Liu X L et al.: "Functionalized chalcones with basic functionalities have antibacterial activity against drug sensitive *Staphylococcus aureus*", European Journal of Medicinal Chemistry, Editions Scientifique Elsevier, Paris, FR, vol. 43, No. 8, Aug. 1, 2008, pp. 1681-1687.
Starkov, S.P. et al.:"Mechanism of formation, structure, and properties of chelates obtained by the rearrangement of m-methoxyphenyl cinnamate and its 4-alkyl derivatives in presence of boron fluoride", J. Gen. Chem. USSR, vol. 46, 1976, pp. 1573-1576.

(Continued)

*Primary Examiner* — Heidi Reese
(74) *Attorney, Agent, or Firm* — Ladas & Parry LLP

(57) ABSTRACT

The present invention relates to the compounds of formula (I):

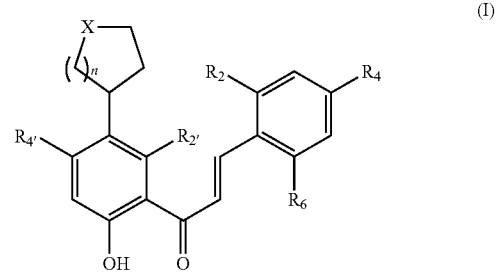

wherein:
$R_2$, $R_4$ and $R_6$, either identical or different, represent a hydrogen, chlorine bromine, iodine or fluorine atom, or a group —OH or —O-alkyl comprising from 1 to 6 carbon atoms;

$R_2'$ and $R_4'$, either identical or different, represent a hydrogen atom, or a group —OH or —O-alkyl comprising from 1 to 6 carbon atoms; with $R_2'$ and/or $R_4'$ which represent a methoxy group;

n is equal to 1, 2, 3;

$X=CH_2$, O, S or $N(R_7)$; and $R_7$ represents a hydrogen atom or an alkyl group comprising from 1 to 6 carbon atoms;

as well as pharmaceutically acceptable hydrates, solvates and salts thereof.

11 Claims, 5 Drawing Sheets

(56) References Cited

OTHER PUBLICATIONS

Starkov, S. P. et al.: "Synthesis and reactions of 5'-sec- and 5'-tert-alkyl-2', 4'-dihydroxychalcones", Izvestiya Vysshikh Uchebnykh Zavedenii, Khimiya I Khimicheskaya Teknologiya, vol. 15, No. 6, 1972, pp. 870-873.

* cited by examiner

CHALCONE DERIVATIVES HAVING AN ANTI-ALLERGIC ACTIVITY

This application is a 371 of PCT/FR2014/050816, filed on Apr. 4, 2014, which claims priority to French Application No. 1353091, filed Apr. 5, 2013.

The present invention relates to novel chalcone derivatives having anti-allergic activity, as well as to pharmaceutical compositions containing such compounds and to such compounds for their use as drugs, and in particular as an anti-allergic drug.

Many studies have already been carried out on chalcone derivatives. As an illustration, mention may be made of the publications of Starkhov S. P. corresponding to XP 0009171181 and XP 009171188, which describe certain chalcone derivatives, without specifying any activity thereof. Different activities have already been reported for chalcone derivatives. Mention may be made of U.S. Pat. No. 6,462,075 which describes chalcone derivatives having an activity inhibiting angiogenesis. These compounds are presented as being used as anti-tumoral, anti-cancer, agents for treating angiogenic diseases of the skin and chronic inflammatory diseases. The publication of X. L. Liu in Eur. J. Med. Chem., 43 (2008), 1681-1687, describes chalcone derivatives presented as antibacterial agents against *Staphylococcus Aureus*.

The patent application WO 2007/083060, as for it, describes a chalcone family having an anti-mitotic activity, results being shown on a cycle test corresponding to the analysis of blocking in phase G2/M a line of human leukemia cells, evaluated by flow cytometry. Although it is mentioned in this patent application that the described compounds may be used for treating secondary signs with connective hypersensitivity, for example rhinitis and allergic asthma, eczema, drug allergies, the inventors of the present patent application have tested several of the compounds described, on the degranulation of normal human basophils and the tested compounds did not show any activity. These results will be presented subsequently in the examples.

Document WO 01/98291 as for it describes a great family of compounds of the chalcone type, shown as being useful for treating disorders mediated by VCAM-1 ("vascular cell adhesion molecule-1"). Among the long list of mentioned pathologies, appear certain allergic diseases. In order to check the activity of the compounds described in the treatment of allergies, among the 655 examples given in this patent application, the inventors of the present patent application have tested the compound described on page 97 of this document, under reference 8 and, the compound described on page 137 under reference 359, in order to check whether they had an activity, at 100 μM, on the degranulation of normal human basophils CD 63 according to the procedure described from page 12 of the present patent application, which is a recognized model for evaluating anti-allergic activity (Clin Mol Allergy. 2005 June 30; 3:9. The basophil activation test by flow cytometry: recent developments in clinical studies, standardization and emerging perspectives. Boumiza R, Debard A L, Monneret G.). Both of these compounds may be considered as inactive, considering the obtained results and shown in the comparative examples of the present patent application.

According to the present invention, the inventors now developed a novel series of chalcones having a benefit in the treatment of allergic diseases.

In this context, the invention relates to the compounds of formula (I):

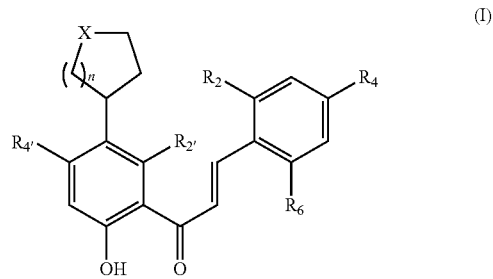

wherein:

$R_2$, $R_4$ and $R_6$, either identical or different, represent a hydrogen, chlorine, bromine, iodine or fluorine atom, or a group —OH or —O-alkyl comprising from 1 to 6 carbon atoms;

$R_2'$ and $R_4'$, either identical or different, represent a hydrogen atom, or a group —OH or —O-alkyl comprising from 1 to 6 carbon atoms; with $R'_2$ and/or $R'_4$ which represent a methoxy group;

n is equal to 1, 2 or 3;

X=$CH_2$, O, S or N($R_7$); and $R_7$ represents a hydrogen atom or an alkyl group comprising from 1 to 6 carbon atoms;

as well as their pharmaceutically acceptable salts, hydrates, solvates.

According to preferred aspects of the invention, the compounds of formula (I), optionally as pharmaceutically acceptable salts, hydrates or solvates, having any of the features hereafter or a combination of several of these features, or even all these features:

X=N($R_7$); in particular, $R_7$ represents a methyl group;

n=2;

$R_2'$ and $R_4'$ are different from hydrogen; in particular $R_2'$ and $R_4'$ represent a methoxy group;

at least two of the groups $R_2$, $R_4$ and $R_6$, and notably $R_2$ and $R_6$, are different from hydrogen;

$R_2$, $R_4$ and $R_6$, either identical or different represent a hydrogen atom, a chlorine atom or a methoxy group.

In all the compounds of formula (I), the configuration around the double bond $\alpha,\beta$ is trans as indicated on the structural formula (I).

By alkyl group, is meant a linear or branched saturated hydrocarbon chain. As examples of an alkyl group comprising from 1 to 6 carbon atoms, mention may notably be made of methyl (noted as Me), ethyl, n-propyl, iso-propyl, n-butyl, tert-butyl, sec-butyl, n-pentyl, n-hexyl groups.

The compounds of formula (I), hereafter, wherein $R_7$=methyl, as well as their pharmaceutically acceptable hydrates, solvates or salts are particularly preferred. In particular, the invention relates to the compounds:

2'-Hydroxy-2,4,6,4',6'-pentamethoxy-5-(1-methylpiperidin-4-yl)chalcone, compound (I.1)

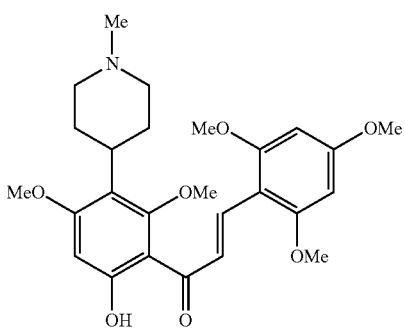 [SMILES: COc1cc(OC)c(/C=C/C(=O)c2c(O)cc(OC)c(C3CCN(C)CC3)c2OC)c(OC)c1]

2'-Hydroxy-2,6,4',6'-tetramethoxy-5-(1-methylpiperidin-4-yl)chalcone, compound (I.2)

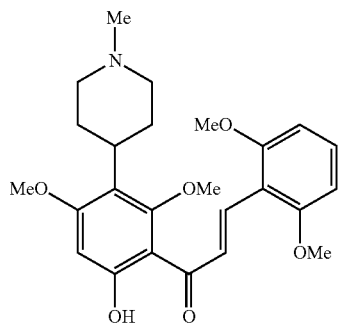 [SMILES: COc1cccc(OC)c1/C=C/C(=O)c1c(O)cc(OC)c(C2CCN(C)CC2)c1OC]

2,6-Dichloro-4',6'-dimethoxy-2'-hydroxy-5-(1-methylpiperidin-4-yl)chalcone, compound (I.3)

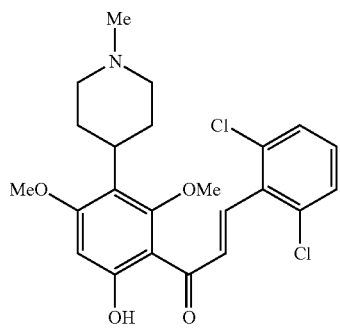 [SMILES: COc1cc(O)c(C(=O)/C=C/c2c(Cl)cccc2Cl)c(OC)c1C1CCN(C)CC1]

as well as their pharmaceutically acceptable hydrates, solvates or salts.

A molecular modeling study was conducted and notably shows that the presence of the nitrogen-containing heterocycle is determining for the anti-allergic activity.

The invention also relates to the compounds defined within the scope of the invention for their use as a drug, and in particular for their use as an anti-allergic drug. Such a use is preferably applied in human beings.

The salts of the compounds according to the invention are prepared according to techniques well known to one skilled in the art. The salts of the compounds of formula (I) according to present invention comprise those with mineral or organic acids which allows suitable separation or crystallization of the compounds of formula (I), as well as of the pharmaceutically acceptable salts. As a suitable acid, mention may be made of: picric acid, oxalic acid or an optically active acid, for example tartaric acid, dibenzoyltartaric acid, mandelic acid or camphor-sulfonic acid and those which form physiologically acceptable salts, such as hydrochloride, hydrobromide, sulfate, hydrogensulfate, dihydrogenphosphate, maleate, fumarate, 2-naphthalenesulfonate, para-toluenesulfonate.

As compounds in hydrated form, mention may be made as examples of semi-hydrates, monohydrates and polyhydrates.

By solvate is meant a form of the compound associated with one or several solvent molecules, notably used during its synthesis or during its purification, without however being in solution in the latter.

When a compound according to the invention has one or several asymmetrical carbons, the optical isomers of this compound are an integral part of the invention. The present invention comprises the compounds of formula (I) in the form of pure isomers but also in the form of a mixture of isomers in any proportion. The compounds (I) are isolated as pure isomers by conventional separation techniques, for example it is possible to use fractionated recrystallizations of a salt of the racemic with an optically active acid or base, the principle of which is well known or the conventional techniques of chromatographies on a chiral or non-chiral phase.

The functional groups optionally present in the molecule of the compounds of formula (I) and in the reaction intermediates may be protected, either permanently, or temporarily, with protective groups which ensure a unique synthesis of the expected compounds. The protection and deprotection reactions are conducted according to techniques well known to one skilled in the art. By temporary protective group of amines, alcohols or carboxylic acids, are meant protective groups such as those described in Protective Groups in Organic Synthesis, Greene T. W. and Wuts P. G. M., ed John Wiley and Sons, 1991 and in Protecting Groups, Kocienski P. J., 1994, Georg Thieme Verlag.

The compounds of formula (I) according to the invention are obtained by aldol condensation of an acetophenone of formula (II) and of a benzaldehyde of formula (III), as illustrated in the examples.

The object of the present invention is also the use of the compounds defined within the scope of the invention, for making a drug and preferably a drug intended for treating allergies. In particular, such drugs are intended for treating human beings.

The compounds according to the invention are more particularly suitable for treating a pathology of allergic origin such as pulmonary disorders, like allergic asthma; allergic skin disorders like eczema, drug allergy, reactions upon contact with products of the environment; digestive disorders including food allergies; other mucosal disorders such as rhinitises and conjunctivitises; allergic joint disorders; local and systemic disorders resulting from contact with a food, cosmetic, hygienic product from professional surroundings, medicinal or toxic, microbiota or parasites; disorders of auto-immune diseases; Quincke's oedema.

The anti-allergic activity of the compounds was demonstrated by studying the capability of the compounds according to the invention of inhibiting degranulation of normal human basophils by conducting marking studies in flow cytometry. The compounds according to the invention have a substantial protective activity towards the degranulation of normal human basophils, such that it may be evaluated by the overexpression of CD203c and of CD63 after exposure to an anti-IgE antibody. In particular, the concentration of the compound according to the invention giving the possibility of obtaining a 50% protective effect (with respect to a value of 100% corresponding to the control achieved in the absence of a compound according to the invention) belongs to the range from 1 to 100 micromolar.

On the other hand, unlike the compounds described in application WO 2007/083060, the compounds according to the invention, when they are tested alone, do not have any significant activity on various studied cancer models.

The pharmaceutical compositions comprising a compound according to the invention, in association with at least one pharmaceutically acceptable excipient, are also an integral part of the invention. In such compositions, the compound according to the invention is present in a therapeutically effective amount.

The term of <<treatment>> refers to any therapeutic prophylactic or suppressive measure for a disease or disorder, leading to a desirable clinical effect or to any beneficial effect, notably including the suppression or reduction of one or several symptoms, regression, slowing down or stopping the progression of the disease or of the disorder which is associated therewith.

By <<therapeutically effective amount>>, is meant any amount of a composition which improves one or several of the characteristic parameters of the treated disease.

The compounds of formula (I), their pharmaceutically acceptable salts, solvates and hydrates are not cytotoxic. Because of their activity, the compounds of formula (I) described earlier as well as their salts, solvates and hydrates, may be used for making a drug intended to treat an allergic disease, and in particular a pathology of allergic origin selected from pulmonary disorders, like allergic asthma; allergic skin disorders like eczema, medicinal allergy, contact reactions to products of the environment; digestive disorders including food allergies; other mucosal disorders such as rhinitises and conjunctivitises; allergic articular disorders; local and systemic disorders resulting from contact with a food, cosmetic, hygienic product, from professional surroundings, medicinal or toxic, microbiota or parasites; signs of auto-immune diseases; Quincke's oedema.

The object of the present invention is also pharmaceutical compositions which may be administered to animals and, in particular to humans, containing a therapeutically effective dose of a compound of formula (I), or a pharmaceutically acceptable salt, solvate or hydrate of the latter, and suitable excipient(s) according to the European Pharmacopoeia 7$^{th}$ Edition, notably. The invention therefore relates to pharmaceutical compositions comprising a compound according to the invention, with at least one pharmaceutically acceptable excipient.

The excipients present in the pharmaceutical compositions according to the invention are selected according to the desired pharmaceutical form and the administration method. In the pharmaceutical compositions of the present invention for oral, sublingual, subcutaneous, intramuscular, intravenous, intra-cartilage, topical, intratracheal, intranasal, transdermal, rectal or intraocular administration, the active ingredients of formula (I), in any proportion, or optional salts, solvates and hydrates thereof, may be administered in a dosage unit for administration, mixed with conventional pharmaceutical supports, to animals and to human beings for prophylaxis or treatment of the diseases above. Suitable administration dosage unit forms comprise forms via an oral route, such as tablets, gelatin capsules, powders, granules and oral solutions or suspensions, sublingual, buccal, intratracheal, intranasal administration forms, subcutaneous, intramuscular, intra-cartilage or intravenous administration forms and rectal administration forms. For topical application, it is possible to use the compounds according to the invention in creams, ointments, patches or lotions.

In order to obtain the desired effect, the compound according to the invention will be present in the composition at a therapeutically effective dose. The active ingredient dose for example varies between 0.1 and 100 mg per kg of body weight and per day.

When a solid composition is prepared as tablets, the main active ingredient is mixed with a pharmaceutical carrier, such as gelatin, starch, lactose, magnesium stearate, talcum, gum arabic or the like. Saccharose tablets may be coated with a cellulose derivative, or with other suitable materials or further they may be treated so that they have prolonged or delayed activity and they continuously release a predetermined amount of active ingredient.

A preparation in gelatin capsules is obtained by mixing the active ingredient with a diluent and by pouring the obtained mixture into soft or hard gelatin capsules.

The pharmaceutical compositions containing a compound of formula (I), or of one of its salts, solvates or hydrates, may also appear in liquid form, for example as solutions, emulsions, suspensions or syrups. The suitable liquid supports may for example be water, organic solvents such as glycerol or glycols, as well as their mixtures, in varied proportions, in water.

A preparation in the form of a syrup or elixir or for administration as drops may contain the active ingredient together with a sweetener, a calorie-free agent, an antiseptic, as well as an agent giving taste and a suitable coloring agent. The powders or granules dispersible in water may contain the active ingredient in a mixture with dispersion agents or wetting agents, or suspension agents, like polyvinylpyrrolidone, as well as with sweeteners or taste correctors.

Generally, the same alternatives as those indicated earlier for the compounds (I) are applicable mutatis mutandis to the drugs, compositions and uses applying these compounds.

The examples hereafter, with reference to the appended Figures, give the possibility of illustrating the invention, but do not have any limiting nature.

FIG. 5 shows the response in non-invasive plethysmography at increasing doses of metacholine for the whole of the groups one day after the first OVA challenge.

FIG. 6 shows the concentration of the intra-bronchial infiltrate of the whole of the groups one day after the last OVA challenge.

FIGS. 7 and 8 show the cytologies obtained by flow cytometry analysis in lungs and the LBA of the whole of the groups one day after last OVA challenge.

Figure 9:
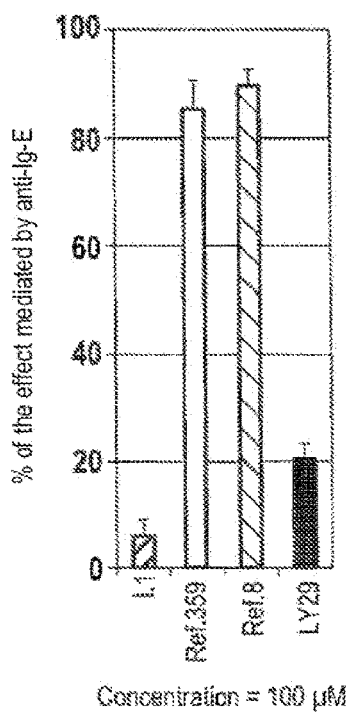
Figure 10:
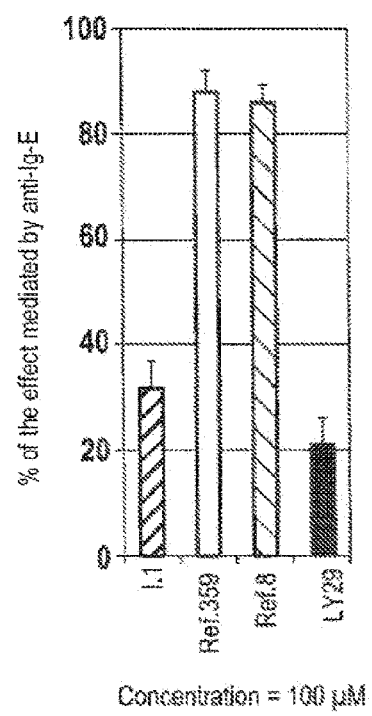

FIGS. 9 and 10 show the results obtained at 100 μM on the degranulation of basophils by flow cytometry, respectively with the CD63 and CD203c markers, for compounds according to the invention and the compound described on page 97 of this document, under reference 8 (noted as Ref. 8 in the Figures) and, the compound described on page 137 under reference 359 (noted as Ref. 8 in the Figures) of WO 01/98291.

I. Synthesis of Chalcones

The chalcones were synthesized according to Scheme 1, hereafter wherein X, n, $R_2$, $R_4$ and $R_6$, $R_2'$ and $R_4'$ are such as defined for the compounds of formula (I), by aldol condensation between an acetophenone derivative (II) and a benzaldehyde derivative (III).

The experimental procedure is the following: To a solution of acetophenone (II) in ethanol or methanol (10 ml/mmol of acetophenone) are successively added the benzaldehyde derivative (III) and a potassium hydroxide solution (KOH, 50% in $H_2O$). The solution is stirred with reflux of the solvent for 24 h. The ethanol or methanol is evaporated and water is added to the remaining residue. The solution is filtered under reduced pressure and the obtained solid is successively washed with water and ether. The purity of the product is analyzed by TLC. The majority of the chalcones were obtained pure at this stage. If TLC reveals the presence of impurities, purification with a chromatography column on silica gel eluted with ethyl acetate/cyclohexane (1/4 to 1/1, v/v) is carried out.

The acetophenone derivatives required for the preparation of the chalcones were synthesized according to the method described in: Liu et al. *Bioorganic & Medicinal Chemistry*, 2007, 15, 7021-7034. The benzaldehyde derivatives are commercial products.

Scheme 1. Scheme for synthesis of chalcones

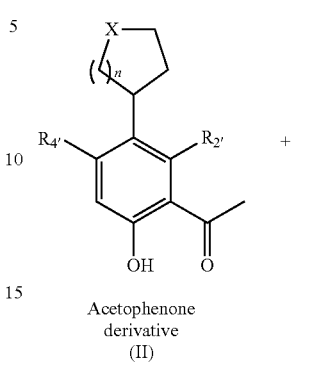

TABLE 1

Structures and characterizations of the reagents and chalcones used.

| Chalcone (I) | Acetophenone derivative (II) | Benzaldehyde derivative (III) | Analytical data of the studied chalcones |
|---|---|---|---|
| 2'-Hydroxy-2,4,6,4',6'-pentamethoxy-5-(1-methylpiperidin-4-yl)chalcone, compound (I.1) | | | 60%, 1H NMR: d 14.55 (s, 1H); 8.24 (d, J = 16 Hz, 1H); 8.20 (d, J = 16 Hz, 1H); 6.14 (s, 2H); 5.98 (s, 1H); 3.95-3.86 (4s, 15 H); 3.19-3.13 (m, 1H); 2.95-2.92 (m, 2H); 2.49-2.40 (m, 2H); 2.30 (s, 3H); 2.10-2.0 (m, 2H); 1.52-1.49 (m, 2H). MS (ESI) m/z 472 (M + H)+. |
| 2'-Hydroxy-2,6,4',6'-tetramethoxy-5-(1-methylpiperidin-4-yl)chalcone, compound (I.2) | | | 35%; 1H NMR: NMR: ethoxy-5-(1-methylpiperidin J = 16 Hz, 2H); 7.24 (t, J = 7 Hz, 1H); 6.58 (d, J = 7 Hz, 2H), 5.99 (s, 1H); 3.99-3.90 (4s, 12H); 3.25-3.15 (m, 1H); 3.0-2.95 (m, 2H); 2.54-2.45 (m, 2H); 2.35 (s, 3H); 2.15-2.0 (m, 2H); 1.53-1.50 (m, 2H). MS (ESI) m/z 442 (M + H)+. |
| 2,6-Dichloro-4',6'-dimethoxy-2'-hydroxy-5-(1-methylpiperidin-4-yl)chalcone, compound (I.3) | | | 30%; 1H NMR: NMR: se (I.3)ose (I.3)hoJ = 16 Hz, 1H); 7.85 (d, J = 16 Hz, 1H); 7.37 (d, J = 8 Hz, 2H); 7.17 (t, J = 8 Hz, 1H); 5.97 (s, 1H); 3.90 (s, 3H); 3.89 (s, 3H); 3.20-3.17 (m, 1H); 2.98-2.96 (m, 2H); 2.50-2.45 (m, 2H); 2.33 (s, 3H); 2.10-2.04 (m, 2H); 1.51-1.48 (m, 2H). MS (ESI) m/z 450 (M + H)+. |

II. Biological Activity a) Activity on the Degranulation of Normal Human Basophils CD203c and CD 63

This test consists of analyzing with flow cytometry the expression of the membrane markers CD203c and CD63 on normal human basophils. For this blood from healthy donors is exposed to an antibody directed against immunoglobulins E (IgE) which leads to activation and degranulation of the basophils, causing an increase in the expression of CD203c and CD63. In order to demonstrate the protective effect of the derivatives of interest, the latter are co-incubated with the basophils and the anti-IgE antibody and the samples are analyzed in order to show a lower level of expression of CD203c and of CD63. As the compounds of interest are dissolved in dimethylsulfoxide (DMSO), a control is also produced by incubating the basophils in the presence of DMSO without any active ingredient.

The activity of the compounds (I.1), (I.2) and (I.3) was compared with the compounds of the prior art notably described in patent application WO2007/083060, as well as with compounds of similar structure synthesized by the inventors, but not having been the subject of prior publications. The different tested comparative examples are shown in Table 2.

TABLE 2

| Comparative Example | Structural formula |
|---|---|
| 1 | 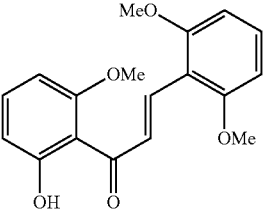 [SMILES: COc1cccc(OC)c1/C=C/C(=O)c1c(O)cccc1OC] |
| 2 | 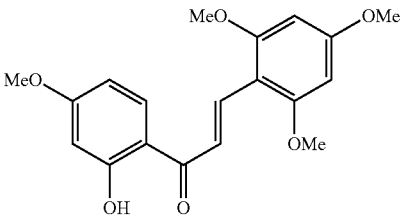 [SMILES: COc1ccc(C(=O)/C=C/c2c(OC)cc(OC)cc2OC)c(O)c1] |
| 3 | 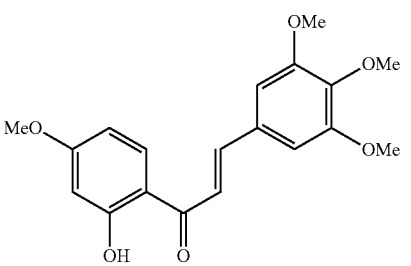 [SMILES: COc1ccc(C(=O)/C=C/c2cc(OC)c(OC)c(OC)c2)c(O)c1] |
| 4 | 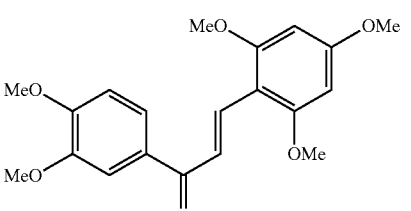 |
| 5 | 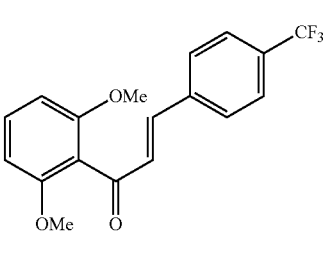 [SMILES: COc1cccc(OC)c1C(=O)/C=C/c1ccc(C(F)(F)F)cc1] |
| 6 | 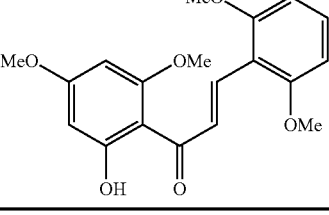 |

Figure 1:
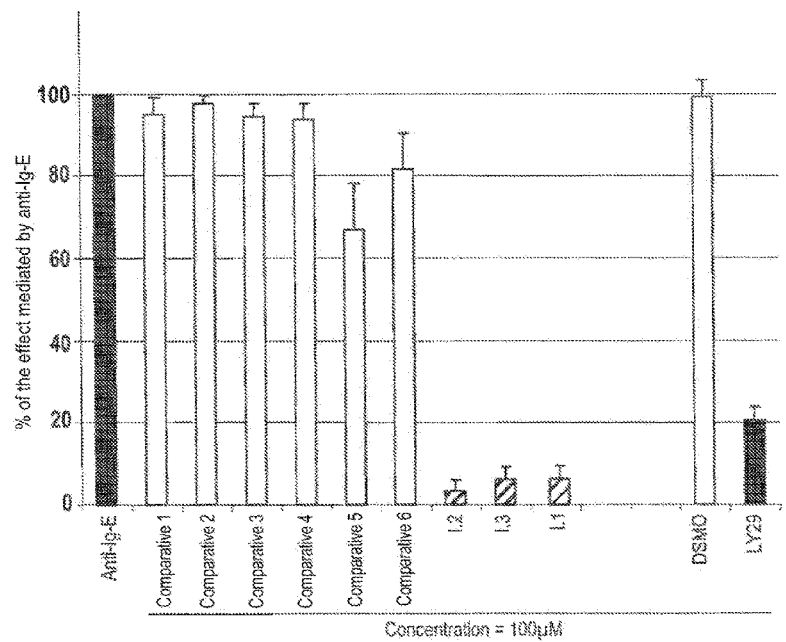
FIGS. 1 and 2 show the results obtained at 100 μM on the degranulation of basophils by flow cytometry, respectively with the markers CD63 and CD203c for compounds according to the invention and other compounds of similar structure.
Figure 2:
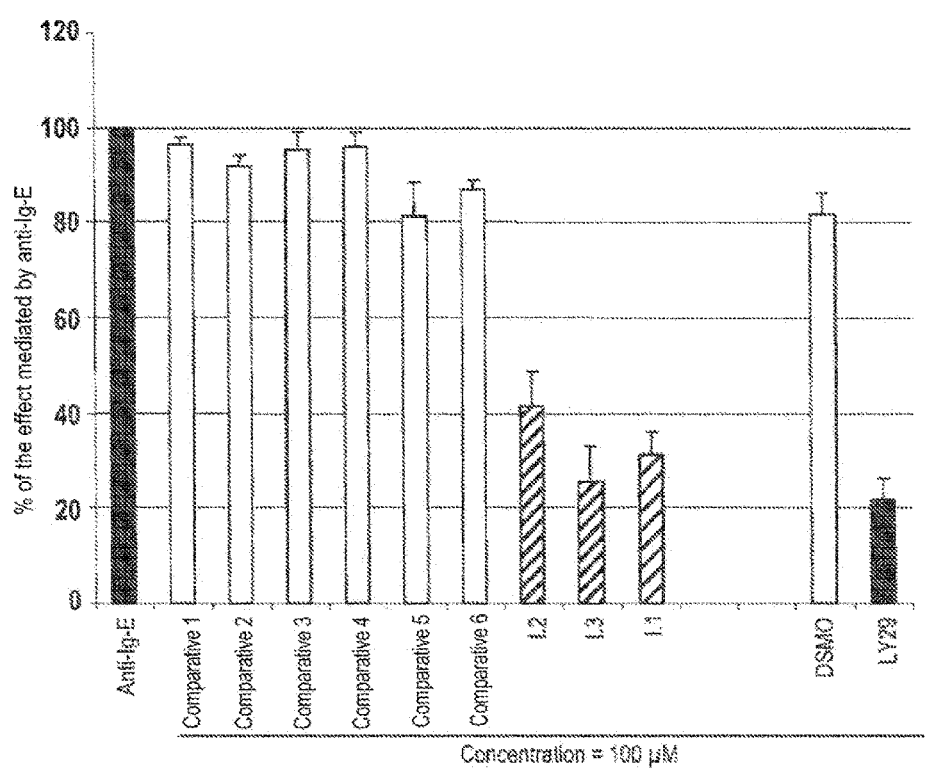

The results obtained at 100 μM on the degranulation of basophils by flow cytometry with the CD63 and CD203c markers are respectively shown in FIGS. 1 and 2. The conducted study shows in both cases, an inhibiting effect of the compounds according to the invention, unlike the other tested compounds.

The inventors of the present patent application have also reproduced the compound described on page 97 of WO 01/98291, under reference 8 and, the compound described on page 137 under reference 359, in order to check that they had an activity, at 100 μM, on the degranulation of normal human basophils CD63 by using the same procedure. The obtained results are shown in FIG. 9 (results on CD63) and 10 (results on CD203c) and show that both of these compounds may be considered as inactive, considering the obtained results, as compared with the compound according to the invention (I.1).

Figure 3:
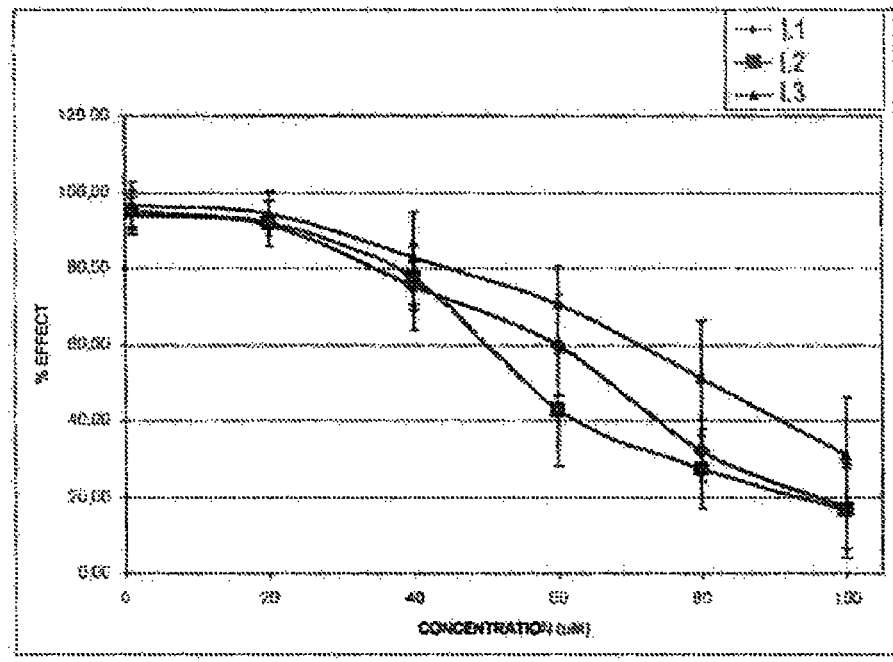
FIGS. 3 and 4 show the results of an effect-dose study conducted with the compounds (I.1), (I.2) and (I.3) on a number of 4 donors, with the markers CD63 and CD203c.
Figure 4:
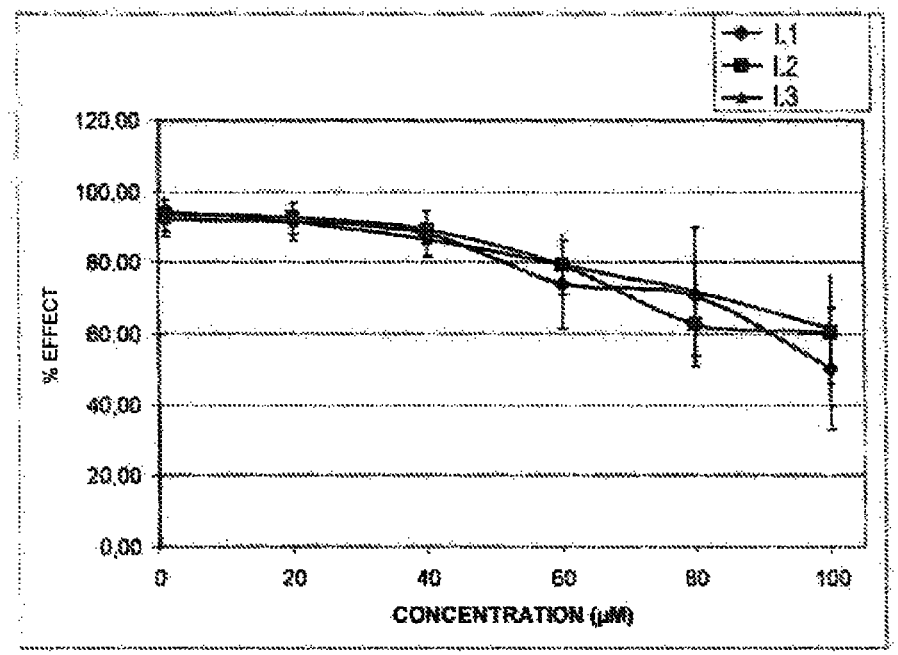

An effect-dose study was also conducted with the compounds (I.1), (I.2) and (I.3) on a number of 4 donors. The results with the CD63 and CD203c markers are respectively shown in FIGS. 3 and 4. A dose effect is observed for both of these markers between 1 and 100 micromolars of compound (I.1), (I.2) or (I.3), without any plateau effect, or significant difference between these compounds. The effect is more pronounced on CD63 (a maximum effect of 80%) than on CD203c (a maximum effect of 40%).

b) Effect on the Respiratory Function in an Asthma Model in Mice

The compounds according to the invention were also subject to tests in vivo. Cromoglycate was used as a reference compound since presently it is the only compound presently marketed having been described as having an effect on the degranulation of basophils.

Reminder of the Procedure:
The model used is an ovalbumin model (ova). The procedure includes:
4 weeks of sensitization with ova solubilized in a solution containing alum and injected intra-peritoneally (I-P).
1 week of challenge with 3 intranasal challenges of ova solubilized in phosphate buffer PBS for 3 subsequent days.
Injections of PBS, of compound (I.1) or of cromoglycate were carried out all along the challenge phase and continued until the date of analysis in an amount of one injection per day intra-peritoneally.
The analyses were carried out 1 and 5 days after the last intranasal challenge.
These analyses comprise:
One Day after the Last Challenge
an analysis the of the respiratory function by non-invasive plethysmography on 10 mice per group. The respiratory function is analysed in response to an increasing dose of metacholine (broncho-constrictor).
recovery and analysis of the broncho-alveolar wash (count of the number of cells, and cytological analysis) on 5 mice.
dissection of the lungs for cytological analysis (microscopic study after staining) on the same 5 mice.
Five Days after the Last Challenge
an analysis of the pulmonary resistance by the forced oscillation technique (invasive method) on the 5 remaining mice of different groups. The pulmonary resistance is analyzed in response to an increasing dose of metacholine (bronchoconstrictor).
recovery and analysis of the broncho-alveolar wash (counting the number of cells, and deposition on a slide by cytospin for cytological analysis) on these 5 mice.
The mice were distributed into 3 groups:
A compound group (1.1) (n=10), an i-cm group (cromoglycate, n=10) and an i-PBS group (n=10).

Administration Method
The compound (I.1) is dissolved in a DMSO solution. This stock solution is then diluted in an ethanol:PBS (vol:vol) solution before intraperitoneal administration. The compound (I.1) is poorly solubilized which may explain the variability observed in certain of the experiments.

Figure 5:
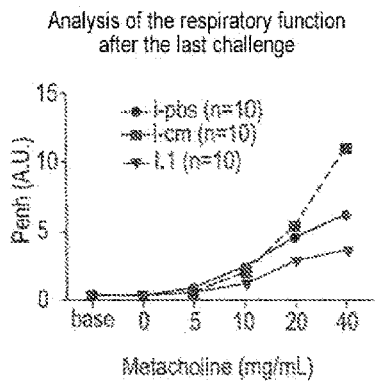
FIGS. 5 to 8 show results obtained with the compound (I.1) in an asthma model in mice.

FIG. 5 shows the response in non-invasive plethysmography at increasing doses of metacholine for the whole of the groups, one day after the last OVA challenge. The Penh (enhanced pause) values, calculated from plethysmography measurements, express the prolongation of the expiratory pause time observed in subjects having a reduction of the bronchial calibre and are correlated with the respiratory resistance. A decrease in the Penh values therefore corresponds to a protective effect towards bronchoconstriction induced by OVA.

Figure 6:
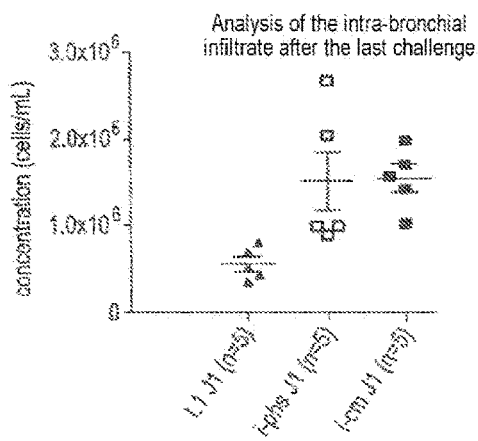

FIG. 6 shows the concentration of the intra-bronchial infiltrate of the whole of the groups, one day after the last OVA challenge.

Figure 7:
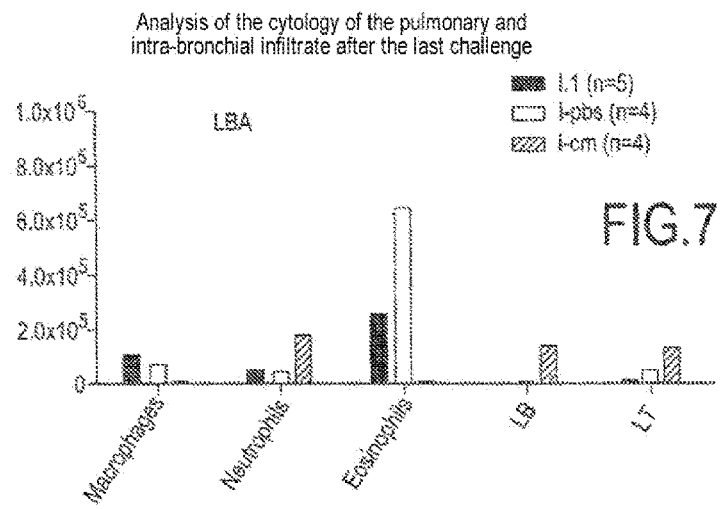
Figure 8:
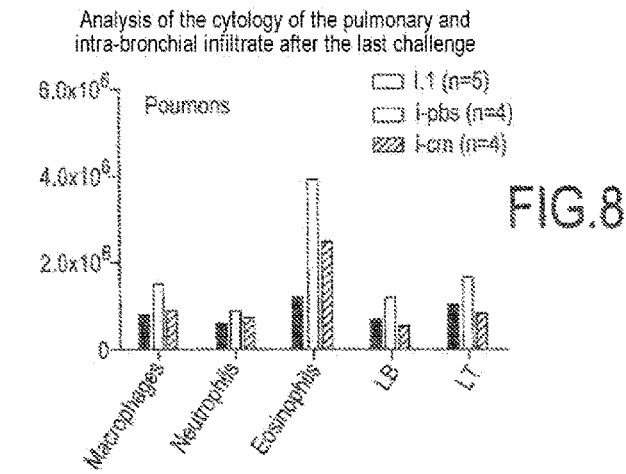

FIGS. 7 and 8 show the cytologies obtained by the flow cytometry analyses in the lungs and the LBA of the whole of the groups one day after the last OVA challenge.

The control group sensitized and challenged with OVA and injected with PBS shows all the signs of asthma allergic to OVA with a high Penh, and this all the more so since the dose of metacholine is significant, a strong intrabronchial infiltrate and strong eosinophilia. This group was used as a reference for the whole of the results.

The analysis of the respiratory function one day after the last OVA challenge shows that cromoglycate and the compound (I.1) lead to different responses. Thus, mice treated with cromoglycate have the same increases in Penh, in response to increasing doses of metacholine than control mice treated with PBS. On the other hand, the difference is significant as soon as dose 20 if this is compared with compound (I.1). If this is compared with the control group injected with PBS, the difference is only significant for the dose at 40 mg/ml.

First conclusion, it therefore seems that one day after the last OVA challenge, the compound (I.1) improves the respiratory function of the mice.

As regards the intrabronchial inflammation, the mice injected with PBS exhibit a significant inflammatory infiltrate. The cromoglycate group does not exhibit any significant difference with the group treated with buffer. On the other hand, the group treated with the compound (I.1) shows a significant decrease in the intrabronchial infiltrate as compared with the PBS and cromoglycate groups. If this is examined at the composition of this infiltrate (FIG. 7), one has a composition which is quite in line with an OVA model with strong eosinophilia and not much increase in the other cell types.

Several Points are of Interest:

First of all, the infiltrate of the PBS group is in line between the various examined parameters. Hypereosinophilia is well correlated with the increase of the intrabronchial infiltrate and with bronchial hyperreactivity. As regards the group of the compound (I.1), a reduction in the eosinophils and T lymphocytes is observed as compared with the PBS group, which correlates well with the reduction of bronchial hyperreactivity. The cromoglycate group, as for it does not show any significant reduction in the eosinophil infiltrate as compared with the PBS group.

As a conclusion, the compound (I.1) seems to act on eosinophilia.

The intra-pulmonary inflammation does not show large variations as compared with the intrabronchial infiltrate. One has hypereosinophilia for all the groups, but the latter is much less substantial in the group of the compound (I.1) including for the cromoglycate group with a reduction of these eosinophils in the group of the compound (I.1).

The whole of these results show that the compound (I.1) induces protection of the mice against bronchoconstriction in this asthma model, induced by OVA and that this protection is accompanied by a reduction of the biological signs of inflammation, both at the pulmonary parenchyma and of the bronchiole/alveolar washing liquid. Remarkably, the compound (I.1) very significantly reduces the eosinophilic infiltrate caused by OVA in this model.

The invention claimed is:

1. A compound of formula (I):

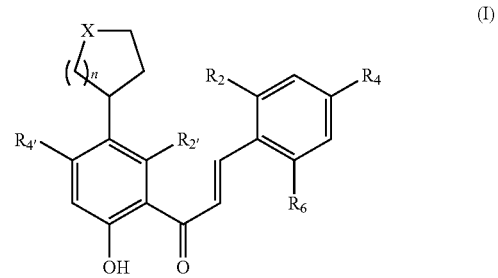

wherein:

$R_2$, $R_4$ and $R_6$, either identical or different, represent a hydrogen, chlorine, bromine, iodine, or fluorine atom, or a group —OH or —O-alkyl comprising from 1 to 6 carbon atoms;

$R_2'$ and $R_4'$ both represent a methoxy group; or $R_2'$ represents a methoxy group and $R_4'$ represents a hydrogen atom, or a group —OH, or —O-alkyl comprising from 2 to 6 carbon atoms; or $R_4'$ represents a methoxy group and $R_2'$ represents a hydrogen atom, or a group —OH, or —O-alkyl comprising from 2 to 6 carbon atoms;

n is equal to 1, 2, 3;

X=N($R_7$); and $R_7$ represents a hydrogen atom or an alkyl group comprising from 1 to 6 carbon atoms;

as well as pharmaceutically acceptable hydrates, solvates and salts thereof.

2. The compound of claim 1, wherein $R_7$ represents a methyl group.

3. The compound of claim 1, wherein n=2.

4. The compound of claim 1, wherein $R_2$, $R_4$ and $R_6$, either identical or different, represent a hydrogen atom, a chlorine atom, or a methoxy group.

5. The compound of claim 1, wherein $R_2'$ and $R_4'$ both represent a methoxy group.

6. The compound of claim 1 selected from the group consisting of:

2'-Hydroxy-2,4,6,4',6'-pentamethoxy-5-(1-methylpiperidin-4-yl)chalcone, compound (I.1)

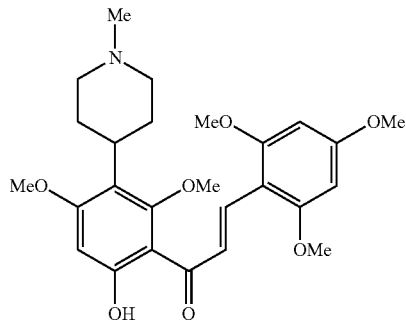 [SMILES: COc1cc(OC)c(/C=C/C(=O)c2c(O)cc(OC)c(C3CCN(C)CC3)c2OC)c(OC)c1]

2'-Hydroxy-2,6,4',6'-tetramethoxy-5-(1-methylpiperidin-4-yl)chalcone, compound (I.2)

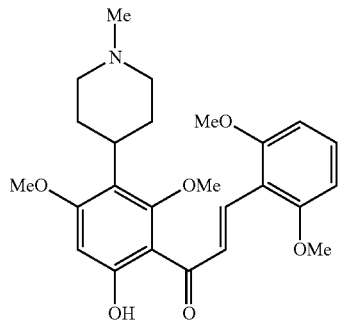 [SMILES: COc1cccc(OC)c1/C=C/C(=O)c1c(O)cc(OC)c(C2CCN(C)CC2)c1OC]

2,6-Dichloro-4',6'-dimethoxy-2'-hydroxy-5-(1-methylpiperidin-4-yl)chalcone, compound (I.3)

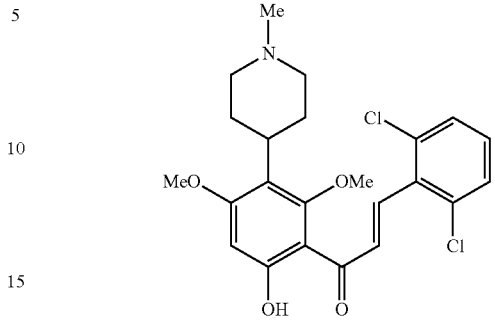

and pharmaceutically acceptable hydrates, solvates and salts thereof.

7. A method of treating an allergic response, the method comprising administering to a subject in need thereof a treatment-effective amount of the compound of claim 1.

8. The method of claim 7, wherein the allergic response is selected from the group consisting of pulmonary disorders; allergic skin disorders; drug allergy; contact reactions to products of the environment; digestive disorders; food allergies; other mucosal disorders; allergic articular disorders; local and systemic disorders resulting from contact with a food, cosmetic, hygienic product from professional surroundings, medicinal or toxic product, microbiota or parasites; auto-immune disease disorders; and Quincke's oedema.

9. The method of claim 8, wherein the allergic response is selected from the group consisting of allergic asthma, rhinitises, and conjunctivitises.

10. The compound of claim 1, wherein:
$R_7$ represents a methyl group;
n=2;
$R_2$, $R_4$ and $R_6$, are either identical or different, an represent a hydrogen atom, a chlorine atom, or a methoxy group; and
$R_2'$ and $R_4'$ both represent a methoxy group.

11. The method of claim 9, wherein the allergic response is allergic asthma.

* * * * *